(12) United States Patent
Oya et al.

(10) Patent No.: US 8,747,634 B2
(45) Date of Patent: Jun. 10, 2014

(54) GAS-SENSOR

(75) Inventors: Seiji Oya, Aichi-ken (JP); Shin Yoshida, Nagaski-ken (JP); Yuko Yamada, Aichi-ken (JP)

(73) Assignee: NGK Spark Plug Co., Ltd., Aichi (JP)

( * ) Notice: Subject to any disclaimer, the term of this patent is extended or adjusted under 35 U.S.C. 154(b) by 210 days.

(21) Appl. No.: 13/045,223

(22) Filed: Mar. 10, 2011

(65) Prior Publication Data

US 2011/0220496 A1 Sep. 15, 2011

(30) Foreign Application Priority Data

Mar. 11, 2010 (JP) .................................. 2010-053926
Mar. 8, 2011 (JP) .................................. 2011-049954

(51) Int. Cl.
*G01N 27/409* (2006.01)
*G01N 27/26* (2006.01)

(52) U.S. Cl.
USPC .......... 204/428; 204/426; 73/23.31; 73/23.32

(58) Field of Classification Search
USPC ................. 204/421–429, 280–296; 73/23.31, 73/23.32
See application file for complete search history.

(56) References Cited

U.S. PATENT DOCUMENTS

| | | | |
|---|---|---|---|
| 4,377,801 A * | 3/1983 | Weber et al. ..................... | 338/34 |
| 6,348,140 B1 | 2/2002 | Matsubara et al. | |
| 7,951,277 B2 * | 5/2011 | Nagao et al. .................. | 204/426 |
| 2006/0113188 A1* | 6/2006 | Mori et al. ..................... | 204/431 |
| 2006/0185978 A1 | 8/2006 | Nagao et al. | |
| 2009/0014330 A1* | 1/2009 | Sugaya et al. ................. | 204/424 |
| 2010/0006433 A1* | 1/2010 | Yasuda et al. ................. | 204/424 |

FOREIGN PATENT DOCUMENTS

| | | |
|---|---|---|
| JP | 01-219662 A | 9/1989 |
| JP | 08-220058 A | 8/1996 |
| JP | 08-278278 A | 10/1996 |
| JP | 09-21782 A | 1/1997 |
| JP | 2000-346827 A | 12/2000 |
| JP | 2005-195516 A | 7/2005 |
| JP | 2006-250925 A | 9/2006 |
| JP | 2007-218893 A | 8/2007 |
| JP | 2009-080111 A | 4/2009 |
| JP | 2009-115781 A | 5/2009 |

OTHER PUBLICATIONS

Hughes et al. (Proc. of SPIE vol. 7212 721203-2), 2009.*
Machine translation of JP 09-021782, performed Oct. 18, 2013.*
Japanese Office Action issued on Sep. 10, 2013 from Japanese Patent Office in Japanese Application No. 2011-049954.
Japanese Office Action issued on Mar. 31, 2014 from the Japanese Patent Office in Japanese Application No. 2011-049954.

* cited by examiner

*Primary Examiner* — Jennifer Dieterle
(74) *Attorney, Agent, or Firm* — Sughrue Mion, PLLC

(57) ABSTRACT

A gas sensor including a gas sensor element, and an inner member surrounding the gas sensor element. The gas sensor element has a detection element having therein a space to which a gas to be measured is introduced, and a heater laminated on the detection element. The detection element includes a first oxygen pumping cell for pumping oxygen into or out of the space, an oxygen concentration detection cell, a detection electrode and a reference electrode. In side faces of the detection element along a laminating direction, a region from a front end of the inner member to a part of the detection electrode along a longitudinal direction is covered with a glass coat having a glass transition point of over 700° C. Further the detection electrode is controlled at a temperature range from 600° C. or more to not more than the glass transition point of the glass coat.

3 Claims, 5 Drawing Sheets

GAS-SENSOR

FIELD OF THE INVENTION

The present invention relates to a gas sensor for detecting the concentration of particular gas components, such as nitrogen oxide ($NO_x$) and oxygen, contained in combustible gas and exhaust gas of a combustion chamber and an internal combustion engine.

BACKGROUND OF THE INVENTION

Conventionally, gas sensors are mounted on, for example, an exhaust system of an engine exhaust pipe or the like and utilized for detecting particular gas components in an exhaust gas. Among these gas sensors, there is known a gas sensor in which a detection element having at least one or more cell provided with a pair of electrodes on a surface of a solid electrolyte body; and a heater are integrally laminated.

In the gas sensor having such a configuration, since a solid electrolyte body is exposed to side faces of a detection element, conductive substances, such as soot, contained in exhaust gas are tend to adhere to the solid electrolyte body. In this case, in the solid electrolyte body to which soot adheres, leak current caused by the soot is generated in a portion achieving the temperature lower than the temperature which burns off the soot (about 600 degrees C.) as well as generating oxygen ion conductivity of the solid electrolyte body (e.g., 200 to 600 degrees C.). As a result, gas concentration detection performance deteriorates.

Thus, a technique has been developed in which a paste mainly made of alumina is applied to an exposed portion of the solid electrolyte body achieving at a temperature of below 600 degrees C. when a gas sensor element is in use (e.g., refer to Patent Document 1).

PRIOR ART DOCUMENT

Patent Document

[Patent Document 1] Japanese Patent Application Laid-Open (kokai) No. 2006-250925

SUMMARY OF THE INVENTION

Problem(s) to be Solved by the Invention

However, when alumina paste is applied to a solid electrolyte body by a printing method, a pinhole is likely to be generated therein. Thus, the alumina paste has to be applied two or more times so as to form a dense insulating layer with no pore on an exposed portion of the solid electrolyte body. This method involves a poor productivity.

Therefore, an object of the present invention is to provide a gas sensor which prevents deterioration in gas concentration detection performance thereof by isolating a portion of an exposed portion of a solid electrolyte body with a glass coat, the portion achieving a temperature lower than the temperature which burns off the soot.

Means for Solving the Problem

In order to solve the above-mentioned problems, there is provided a gas sensor according to the present invention, comprising: a gas sensor element extending in a longitudinal direction and exposed to a gas to be measured at a front end side thereof; a metal casing surrounding a radially outer circumference of the gas sensor element so that the front end side of the gas sensor element projects from a front end of the casing, and an insulating inner member accommodated in the casing and surrounding the radially outer circumference of the gas sensor element, wherein the gas sensor element includes a detection element in which a solid electrolyte body, a detection electrode disposed on the solid electrolyte body and exposed to the gas to be measured and a reference electrode disposed on the solid electrolyte body at an opposing position to the detection electrode are provided, wherein the gas sensor element further includes a heater laminated on the detection element and having therein an heat-generating portion that is disposed at a position corresponding to at least the detection electrode in the longitudinal direction of the detection element, wherein, in side faces of the detection element, a region from a front end of the inner member to at least a part of the detection electrode along the longitudinal direction of the detection element is covered with a glass coat having a glass transition point of over 700 degrees C., and wherein the detection electrode is controlled at a temperature range from 600 degrees C. or more to not more than the glass transition point of the glass coat.

In the present invention, the side faces of the detection element located at a rear end side with respect to the detection electrode and achieving a temperature lower than that of the detection electrode which is controlled by the heater is covered and isolated with the glass coat. Thus, in the portion of the solid electrolyte body, conductive substances contained in exhaust gas, such as soot, do not adhere to the portion achieving a temperature lower than the temperature which burns off the soot as well as generating the oxygen ion conductivity of the solid electrolyte body (200 to 600 degrees C.). As a result, any leak current caused by conductive substances, such as soot, can be prevented, and the gas concentration detection performance can be maintained. Notably, the "leak current" is caused by conductive substances, such as soot, and generates a phenomenon that electrical conduction is established between the detection element and the metal casing.

Further, glass slurry for forming the glass coat is applied to the detection element (gas sensor element) after firing, and thereafter, it is fired with the detection element (gas sensor element). Since the glass slurry has fluidity performance even at the firing process, an excellent leveling is achieved. As a result, no open pore (which communicates to the side faces of the detection element) is formed even in a single application of the slurry, thereby improving the productivity.

Furthermore, when comparing at the same temperature, the glass coat has smaller thermal expansion coefficient than that of an alumina coat, whereby the glass coat is less likely to cause distortion of the detection element at the time of firing or when a gas sensor is in use.

Moreover, when the glass transition point of the glass coat is over 700 degrees C., a crack in the glass coat caused by increase in thermal expansion occurred due to its transition to a supercooled liquid, or a corruption of the glass coat due to glass melting caused by a reaction with impurities (such as an alkali metal, Pb, P and Zn) can be prevented even if the solid electrolyte body is heated at 600 degrees C. or more which is in a temperature range that can burn off the conductive substances, such as soot contained in a gas to be measured.

Also, since the detection electrode is controlled at a range of 600 degrees C. or more to not more than the glass transition point of the glass coat, the operation of the solid electrolyte body is stabilized, as well as burning off the conductive substances, such as soot, contained in the gas to be measured. Moreover, since the glass coat is maintained at not more than the glass transition point, the glass coat is unlikely to be removed from the original position (i.e., it moves from the original position because the glass coat is softened and runs).

A gas sensor according to the present invention, comprising: a gas sensor element extending in a longitudinal direction and exposed to a gas to be measured at a front end side thereof; a metal casing surrounding a radially outer circumference of the gas sensor element so that the front end side of the gas sensor element projects from a front end of the casing, and an insulating inner member accommodated in the casing and surrounding the radially outer circumference of the gas sensor element, wherein the gas sensor element includes a detection element having therein a space which communicates to an exterior of the gas sensor element and to which a gas to be measured is introduced, and a heater laminated on the detection element and having therein an heat-generating portion that is disposed at a position corresponding to a detection electrode in the longitudinal direction of the detection element, wherein the space is formed between a first solid electrolyte body and a second solid electrolyte body, wherein the detection element includes: a first oxygen pumping cell provided with a first solid electrolyte body and a pair of first pump electrodes disposed on the first solid electrolyte body and in which one of the first pump electrodes is exposed to the space, and the first oxygen pumping cell used for pumping oxygen in or out of the space; and an oxygen concentration detection cell provided with the second solid electrolyte body, the detection electrode disposed on the second solid electrolyte body and exposed to the space, and a reference electrode disposed at an opposing position to the detection electrode, and the oxygen concentration detection cell generating an electric motive force between the reference electrode and the detection electrode, wherein, in side faces of the detection element, a region from a front end of the inner member to at least a part of the detection electrode along a longitudinal direction of the detection element is covered with a glass coat having a glass transition point of over 700 degrees C., and wherein the detection electrode is controlled at a temperature range from 600 degrees C. or more to not more than the glass transition point of the glass coat.

Thus, in the detection element (gas sensor) having a plurality of solid electrolyte bodies according to the present invention, the side faces of the detection element located at a rear end side with respect to the detection electrode and achieving the temperature lower than that of the detection electrode which is controlled by the heater is covered and isolated by the glass coat. Thus, in the portion of the solid electrolyte body, conductive substances contained in the exhaust gas, such as soot, do not adhere to the portion achieving a temperature lower than the temperature which burns off the soot as well as generating the oxygen ion conductivity of the solid electrolyte body (200 to 600 degrees C.). As a result, any leak current caused by conductive substances, such as soot, can be prevented, and also the gas concentration detection performance can be maintained. Notably, in the detection element (gas sensor) which has a plurality of solid electrolyte bodies, the "leak current" is caused by conductive substances, such as soot, and generates a phenomenon that electrical conduction is established between not only the detection element and the metal casing, but also the solid electrolyte bodies (the first solid electrolyte body and the second solid electrolyte body).

Further, glass slurry for forming the glass coat is applied to the gas sensor element after firing, and thereafter, it is fired with the detection element (gas sensor element). Since the glass slurry has the fluidity performance even at the firing process, an excellent leveling is achieved. As a result, no open pore (which communicates to the side faces of the detection element) is formed even in a single application of the slurry, thereby improving the productivity.

Furthermore, when comparing at the same temperature, the glass coat has smaller thermal expansion coefficient than that of an alumina coat, whereby the glass coat is less likely to cause distortion of the detection element at the time of firing or when a gas sensor is in use.

Moreover, when the glass transition point of the glass coat is over 700 degrees C., a crack in the glass coat caused by increase in thermal expansion occurred due to its transition to a supercooled liquid, or a corruption of the glass coat due to glass melting caused by a reaction with impurities (such as an alkali metal, Pb, P and Zn) can be prevented even if the solid electrolyte body is heated at 600 degrees C. or more which is in a temperature range that can burn off the conductive substances, such as soot contained in a gas to be measured. Also, since the detection electrode is controlled at a range of 600 degrees C. or more to not more than the glass transition point of the glass coat, the operation of the solid electrolyte body is stabilized, as well as burning off the conductive substances, such as soot, contained in the gas to be measured. Moreover, since the glass coat is maintained at not more than the glass transition point, the glass coat is unlikely to be removed from the original position (i.e., it moves from the original position because the glass coat is softened and runs).

The detection element includes: a measuring chamber communicating to the space, and to which a gas to be measured is introduced from the space where oxygen has been pumped in or pumped out; a second oxygen pumping cell provided with a third solid electrolyte body facing a part of the measuring chamber and a pair of second pump electrodes in which one of the second pump electrodes is exposed to the measuring chamber formed on the third solid electrolyte body and the other the second pump electrode is located outside of the measuring chamber, and wherein the glass coat preferably has no open pore therein.

Thus, the gas sensor element including the second oxygen pumping cell in addition to the first oxygen pumping cell and the oxygen concentration detection cell has a tendency that the current flowing into the pair of second pump electrodes of the second oxygen pumping cell becomes minute. Therefore, when the conductive substances, such as soot, adhere to the side faces of the detection element (solid electrolyte body) and the leak current is generated, the current flowing into the pair of second pump electrodes receive relatively large influence. Thus, in the present invention, forming the glass coat with no open pore on the side faces of the detection element including three cells, it is possible to prevent the conductive substances, such as soot, from adhering to the side faces of the detection element, whereby the generation of the leak current interfering the current flowing into the pair of second pump electrodes is prevented.

The glass coat preferably contains Li, Na, K, Rb, Cs and Pb at a rate of 3000 mass ppm or less, respectively, more preferably, 3000 mass ppm or less in total, most preferably, these components are not included in the glass coat. When any one of these elements is contained at a rate of over 3000 mass ppm, the insulation performance and heat resistance of the glass coat may fall. When these elements are not contained at all, deterioration in insulation performance and heat resistance performance is less likely to occur.

A porous insulating ceramic layer is preferably formed on the front end portion of the glass coat so as to externally cover the surface of the gas sensor element and that of the glass coat.

In this way, by externally covering the front end portion of the glass coat with the insulating ceramic layer, the glass coat can be prevented from being peeled off from the front end portion thereof.

Effect of the Invention

According to the present invention, in the exposed portion of the solid electrolyte body, the portion achieving the temperature lower than the temperature which can burn off the soot can be prevented from conductive substances, such as soot, that adhere to the solid electrolyte body by isolating the portion with the glass coat. As a result, deterioration in gas concentration detection performance of the gas sensor is prevented.

MODE FOR CARRYING OUT THE INVENTION

Hereafter, an embodiment of the present invention will be described.

Hereafter, the embodiment of the present invention will be described.

Figure 1:
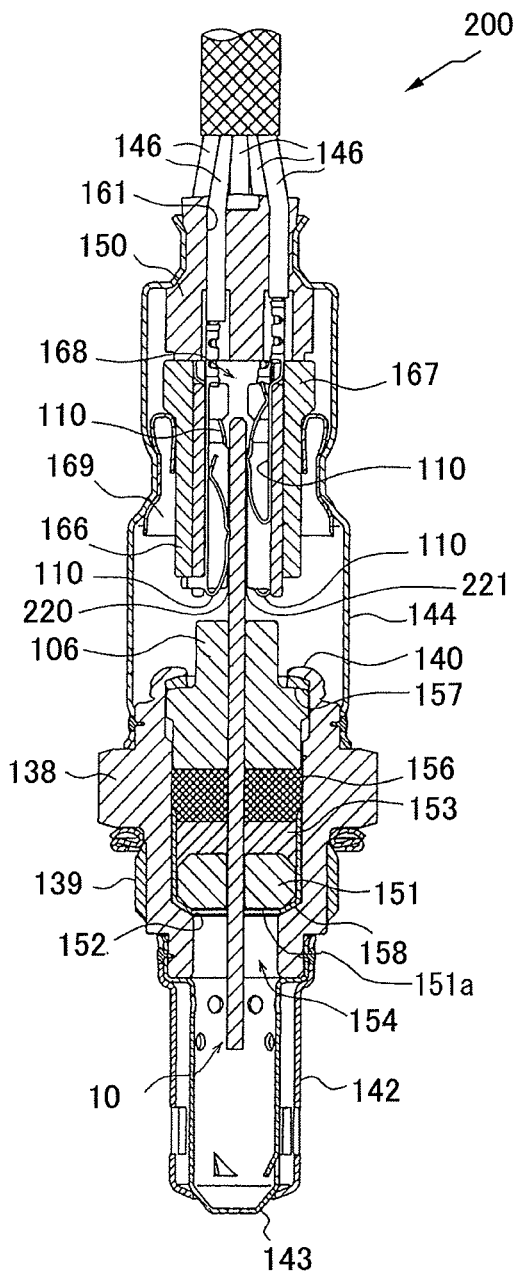
FIG. 1 is a sectional view of a $NO_x$ sensor in a longitudinal direction according to a first embodiment of the present invention.
Figure 2:
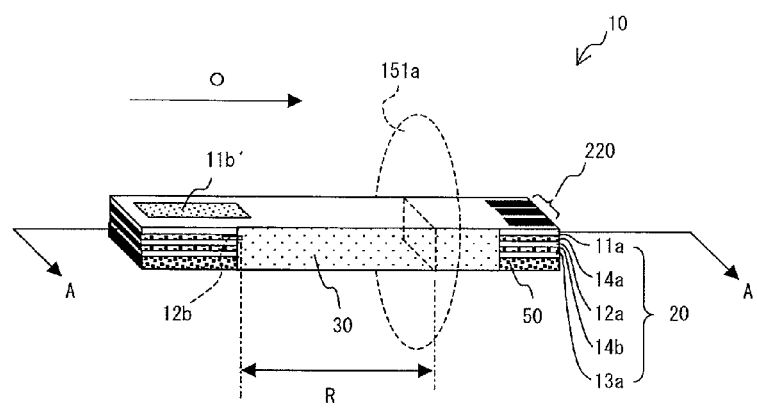
FIG. 2 is a perspective view of a $NO_x$ sensor element.
Figure 3:
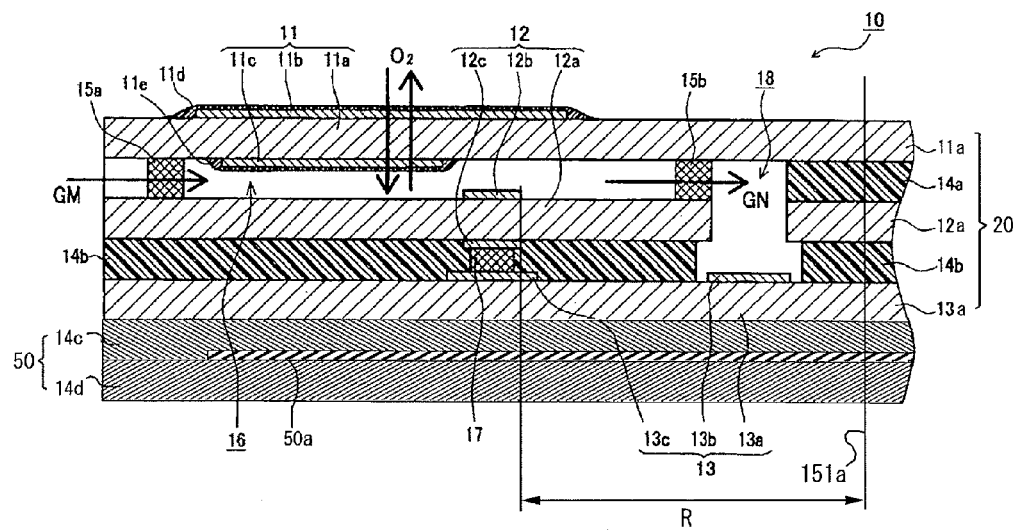
FIG. 3 is a sectional view of a front end portion of a $NO_x$ sensor element taken along A-A line of FIG. 2 (sectional view in a laminating direction of each layer).

FIG. 1 is a sectional view of a $NO_x$ sensor 200 in a longitudinal direction according to a first embodiment of the present invention. FIG. 2 is a perspective view of the $NO_x$ sensor element 10. FIG. 3 is a sectional view of a front end portion of the $NO_x$ sensor element 10 taken along A-A line (along an axial direction) of FIG. 2.

In FIG. 1, a $NO_x$ sensor 200 includes: a cylindrical metallic shell 138 (equivalent to "casing" in claims) having a threaded portion 139 which is formed on the outer surface thereof and adapted to be fixed to the exhaust pipe; a plate-like $NO_x$ sensor element 10 (equivalent to "gas sensor element" in claims) extending in the axial direction (longitudinal direction of the $NO_x$ sensor: the vertical direction in the drawings); a cylindrical ceramic sleeve 106 radially surrounding the $NO_x$ sensor element 10; an insulation contact member 166 disposed in such a manner that an inner wall surface of a contact insertion hole 168 that penetrates in the axial direction surrounds a rear end portion of the $NO_x$ sensor element 10; and six connection terminals 110 (two pieces illustrated in FIG. 1) disposed between the $NO_x$ sensor element 10 and the insulation contact member 166.

The metallic shell 138 is made of stainless steel and is formed into a substantially cylindrical shape. The metallic shell 138 has a through hole 154 extending therethrough in an axial direction and a ledge 152 projecting radially inward in the through hole 154. The $NO_x$ sensor element 10 is disposed in the through hole 154 in such a manner that the front end portion of the $NO_x$ sensor element 10 projects from the front end of the through hole 154. Further, the ledge 152 includes a taper surface inwardly tapered and inclined from a plane perpendicular to the axial direction.

An annular ceramic holder 151 made of alumina and surrounding the circumference of the $NO_x$ sensor element 10 in the radial direction, powder layers 153 and 156 (hereinafter, may be referred to as talc rings 153 and 156), and the ceramic sleeve 106 are stacked in this order from the front end side toward the rear end side in the through hole 154 of the metallic shell 138. The ceramic holder 151 disposed in the frontmost position among the above members and surrounding the radially outer circumference of the $NO_x$ sensor element 10 corresponds to an "inner member" in the claims. A reference numeral 151a represents a front end of the ceramic holder 151.

Further, a crimp packing 157 is disposed between the ceramic sleeve 106 and a rear end portion 140 of the metallic shell 138. A metal holder 158 is disposed between the ceramic holder 151 and the ledge 152 of the metallic shell 138 for holding the talc ring 153 and the ceramic holder 151. The rear end portion 140 of the metallic shell 138 is crimped in such a manner as to press the ceramic sleeve 106 forward via the crimp packing 157. With this configuration, conductive substances, such as soot, are not likely to adhere to a surface of the $NO_x$ sensor element 10 which corresponds to the rear end side with respect to the front end 151a of the ceramic holder 151 even when the $NO_x$ sensor element 10 is exposed to a gas to be measured, such as an exhaust gas.

On the other hand, as shown in FIG. 1, an outer protector 142 and an inner protector 143 are attached to the outer circumference of the front end side (a lower end portion in FIG. 1) of the metallic shell 138 by welding or the like. The protectors 142 and 143 assembled in a dual structure are made of metal (e.g., stainless steel) having a plurality of holes, and cover a projecting portion of the $NO_x$ sensor element 10.

An outer tube 144 is fixed to the outer circumference of the rear end of the metallic shell 138. A grommet 150 is disposed in a rear end (upper end in FIG. 1) opening portion of the outer tube 144. The grommet 150 has lead insertion holes 161 used for accommodating six lead wires 146 (only five lead wires 146 are shown in FIG. 1), respectively. Six lead wires 146 are electrically connected to six electrode terminals 220 and 221 (only two electrode terminals are shown in FIG. 1) of the $NO_x$ sensor element 10, respectively.

The insulation contact member 166 is disposed at the rear end side (upper end portion in FIG. 1) of the $NO_x$ sensor element 10 projecting from the rear end portion 140 of the metallic shell 138. The insulation contact member 166 is disposed around the electrode terminals 220 and 221 formed on the surface of the rear end side of the $NO_x$ sensor element 10. The insulation contact member 166 assumes a cylindrical shape; has the contact insertion hole 168 extending therethrough in the axial direction; and has a flange portion 167 projecting radially outward from the outer surface thereof. A holding member 169 is in contact with the outer tube 144 and the flange portion 167, thereby holding the insulation contact member 166 within the outer tube 144.

As shown in FIG. 2, the $NO_x$ sensor element 10 has a structure in which a first solid electrolyte layer 11a, an insulating layer 14a, a second solid electrolyte layer 12a, an insulating layer 14b, a third solid electrolyte layer 13a, and insulating layers 14c and 14d are laminated together in this order. These layers 11a, 14a, 12a, 14b, 13a and electrodes that are not illustrated constitute a detection element 20.

Further, an outer first pump electrode 11b is formed on an upper surface of a first solid electrolyte layer 11a. A detection electrode 12b is disposed in a location which overlaps with the outer first pump electrode 11b in the axial direction O and is on an upper surface of a second solid electrolyte layer 12a. In addition, on the upper surface of the first solid electrolyte layer 11a, a portion where no outer first pump electrode 11b is disposed is covered with an insulating layer. Furthermore, a heater 50 is laminated on a lower surface of the detection element 20 to thereby constitute the $NO_x$ sensor element 10 as a whole. The heater 50 is comprised of the insulating layers 14c and 14d; and a heat-generating portion not illustrated. In addition, the detailed configuration of the $NO_x$ sensor element 10 will be described later.

Here, the first solid electrolyte layer 11a corresponds to the "first solid electrolyte body" in the claims, and the second solid electrolyte layer 12a corresponds to the "second solid electrolyte body" in the claims.

Each solid electrolyte body used in this embodiment is made of a partially stabilized zirconia sintered body in which C phase, M phase and T phase (cubic, monoclinic and tetragonal phases) are mixed. In this case, a part of each M phase and T phase in the solid electrolyte body is subjected to phase transition between monoclinic (M phase) and tetragonal (T phase) along with a change in volume at 700-1100 degrees C. which causes M/T transformation. At this time, the behavior of thermal expansion coefficient of the solid electrolyte body exhibits a hysteresis (indicated with an arrow) as shown in "solid electrolyte body" of FIG. 4, which will be described later. Notably, in FIG. 4, an upper line of "solid electrolyte body" represents a behavior of thermal expansion coefficient when the solid electrolyte body is heated from a room temperature, and a lower line thereof shows a behavior of the thermal expansion coefficient when the solid electrolyte body is cooled down from a high temperature state.

The thermal expansion coefficient of a conventional alumina coat ("conventional coat" in FIG. 4) is larger than that of the solid electrolyte body (lower line of the solid electrolyte body in FIG. 4) when being cooled down. Thus, the alumina coat is pulled towards the element side when cooling the element, and a crack tends to occur. Thus, the alumina coat has low durability.

On the other hand, the thermal expansion coefficient of a glass coat ("glass coat" in FIG. 4) is smaller than that of the solid electrolyte body ("solid electrolyte body" in FIG. 4) at the temperature range below the glass transition point. Therefore, even when a change in volume of the detection element occurs along with the heating and cooling of the detection element, the glass coat normally receives a force that orients the glass coat to be compressed. Although a ceramic, such as glass and alumina, is strong against a compression force but weak against tensile stress, a crack hardly occurs even when there is a change in volume of the glass coat. As a result, the glass coat has high durability.

Moreover, even though the glass coat is temporarily at a temperature more than a transition point thereof, a viscosity of the glass coat falls and fluidity thereof is kept in such a temperature range. Thus, a crack is unlikely to occur and durability of the glass coat improves.

In FIG. 2, in the side faces of the detection element 20 (i.e., a face along with a laminating direction of the first solid electrolyte layer 11a and the second solid electrolyte layer 12a, and the face in a thickness direction of the solid electrolyte layer when viewed as a whole), a region R from a front end 151a of the ceramic holder 151 to the rear end of the detection electrode 12b in the longitudinal direction (axial direction O) of the detection element 20 is covered with a glass coat 30. More particularly, in this embodiment, the glass coat 30 extends towards the front end side (near the center of the detection electrode 12b) beyond the region R and towards the rear end side of the front end 151a. In addition, the front end 151a of the ceramic holder 151 is located on the rear end side with respect to the outer first pump electrode 11b and the detection electrode 12b.

Moreover, since the detection element 20 and the heater 50 are integrally laminated, the glass coat 30 may be formed in the region R of the side faces of the $NO_x$ sensor element 10, regardless of the detection element 20 and the heater 50. According to this embodiment, as shown in FIG. 2, the glass coat 30 is formed in the region R of the side faces of the $NO_x$ sensor element 10 including the detection element 20 and the heater 50. In addition, the laminating direction represents a direction that penetrates each layer 11a to 13a of the detection element 20, i.e., the vertical direction in FIG. 2.

The glass coat 30 is made of a glass having a glass transition point of over 700 degrees C. The composition of this glass can be an amorphous glass at least containing 40 to 70 wt % $SiO_2$, in total 10 to 45 wt % alkaline earth oxide (one or more types selected from groups of MgO, CaO, SrO, and BaO). As is described later, when an operation temperature of the detection electrode 12b is at 600-700 degrees C., a crack occurs in the glass coat 30 due to its transition to a supercooled liquid because the solid electrolyte layer near the detection electrode 12b has the temperature of about 700 degrees C. or less. Alternatively, the glass coat 30 may melt and corrupts due to a reaction with impurities, resulting in the glass coat being unstable and having a poor heat resistance. In addition, alkaline earth oxide contained in the composition of the glass improves fusibility of glass slurry, as well as preventing deterioration in insulating properties of the glass coat 30.

The glass coat 30 is formed in such a manner that a slurry made of a mixture of glass powder and other components (e.g., sintering modifier) is applied to the side faces of the $NO_x$ sensor element 10, and subsequently, the thus-formed slurry is fired at a predetermined temperature (e.g., 900-1400 degrees C.). The slurry (glass slurry) containing glass component has a excellent leveling at the time of an application, and any pinhole failure is less likely to occur. Thus, a glass coat with no open pore can be obtained in a single application of the glass slurry, which results in better productivity, compared to an alumina paste application. Notably, since a firing temperature of the glass slurry is lower than that of the $NO_x$ sensor element 10, the firing of the glass slurry should be conducted after firing and completing the $NO_x$ sensor element 10.

Although the thickness of the glass coat 30 in the laminating direction is not particularly limited, it may fall within a range from 1/10 to 1/500 of the thickness of the $NO_x$ sensor element 10.

Since, in the side faces of the $NO_x$ sensor element 10 (the detection element 20), at least the region R which achieves the temperature lower than that of the detection electrode 12b, which is controlled by the heater 50, and which is located at the rear end side with respect to the detection electrode 12b is coated with the glass coat 30. Thus, in the side faces of the solid electrolyte layer 11a to 13a, conductive substances contained in the exhaust gas, such as soot, do not adhere to the portion achieving the temperature lower than the temperature which burns off the soot as well as generating oxygen ion conductivity of the solid electrolyte layer (200 to 600 degrees C.). As a result, any leak current caused by conductive substances, such as soot, can be prevented, and the gas concentration ($NO_x$ concentration) detection performance can be maintained.

As will be described later, since the glass coat 30 has thermal expansion coefficient smaller than that of the alumina coat when compared at the same temperature, the glass coat 30 is less likely to cause distortion of the $NO_x$ sensor element 10 (detection element 20) at the time of firing or when the NOx sensor is in use.

In addition, since the heater 50 heats the detection electrode 12b at around an activation temperature of each solid electrolyte layer 11a to 13a, the soot adhered to the portion, which is located on the front end side with respect to the detection electrode 12b, of the detection element 20 is burned off. Thus, each solid electrolyte layer 11a to 13a on the front end side with respect to the detection electrode 12b does not need to be covered with the glass coat 30. Further, in the front end side of the detection electrode 12b, since there is a portion which achieves the temperature near the transition point of the glass coat 30 (more than 700 degrees C.), the glass coat 30 should not be formed on such portion of the side faces of the detection element 20, which the portion achieves at over 700 degrees C.

Therefore, a region for forming the glass coat 30 on the front end side with respect to the detection electrode 12b is preferably defined considering a temperature of the $NO_x$ sensor 200 when used, a resulting temperature on the front end side with respect to the detection electrode 12b, and the glass transition point.

On the other hand, in the side faces of the $NO_x$ sensor element (detection element 20), although a rear end portion with respect to the front end 151a of the ceramic holder 151 does not need to be covered with the glass coat 30, it is preferable that the rear end portion corresponding to the rear end of the ceramic holder 151 be covered with the glass coat 30. In this way, even though soot is invaded between the ceramic holder 151 and the $NO_x$ sensor element 10, no soot adheres to the $NO_x$ sensor element 10. More preferably, the glass coat is formed on a rear end portion of the $NO_x$ sensor element 10 which corresponds to a rear end side of a rear end of the rearmost end member (in FIG. 1, the ceramic sleeve 106) which radially surrounds the $NO_x$ sensor element 10. If the rear end of the glass coat 30 is disposed between the front end 151a of the ceramic holder 151 and the rear end of the ceramic sleeve 106, the rear end of the glass coat 30 serves as a boundary between a non-glass coated portion and a glass coated portion, which generates an unevenness on the element surface. Also, since the $NO_x$ sensor element 10 is supported at this boundary, a stress concentrates on this boundary, resulting in a breakage of the element. However, when the glass coat 30 is formed in the rear end side with respect to the ceramic sleeve 106, the $NO_x$ sensor element 10 has no uneven on the supported portion and has a smooth surface. As a result, no stress is concentrated on any particular portion of the $NO_x$ sensor element 10, and breakage of the element is unlikely to occur.

When the glass coat 30 is measured by the following method, it is preferable that an open pore does not exist therein. As described above, since the glass slurry exhibits an excellent leveling at the time of the application, no open pore (pore which communicates to the side faces of the detection element 20) is generated even in a single application. As a result, the productivity of the sensor element improves compared to a case where the glass coat is applied at plural times. Measuring method for confirming existence/absence of open pore:

(1) The glass coat 30 is formed on the side faces of the $NO_x$ sensor element 10, and thereafter, the heater 50 is energized so that resistance (impedance) of the first solid electrolyte body 12a is to be 100 ohms. Subsequently, after the elapse of 600 seconds from the timing that the resistance of the first solid electrolyte body 12a becomes 100 ohms, a second pump current Ip2 (described later) fed into a second oxygen pumping cell 13 is measured as an offset value.

(2) Next, carbon is sprayed on the side faces of the $NO_x$ sensor element 10 (including the glass coat 30) so that its thickness is to be 1 micrometer or more. This carbon coat contains 10 mass % or more carbon particles, each particle having a size of 1 micrometer or less.

(3) Further, the offset value of the $NO_x$ sensor element 10 after the carbon coat is measured in the similar manner to (1). When the difference in the offset value before and after the carbon coat is less than 0.03 microA, it is considered no open pore exist in the glass coat 30.

The glass coat 30 preferably contains Li, Na, K, Rb, Cs, and Pb at a rate of 3000 mass ppm, respectively, or these components are preferably not included in the glass coat 30. When any one of these components is contained in the glass coat 30 at a rate of over 3000 mass ppm, the insulation performance and heat resistance of the glass coat 30 may deteriorate. In addition, although it is preferable that the glass coat 30 does not include Li, Na, K, Rb, Cs and Pb (0 ppm), these components may be included as inevitable impurities.

The glass coat 30 preferably contains 1 to 50 mass % $Al_2O_3$. When the glass coat 30 contains 1 mass % or more $Al_2O_3$, the insulation of the glass coat 30 improves at a high temperature and heat resistance thereof also improves because of the anchor effect of $Al_2O_3$ particles. When the glass coat 30 includes over 50 mass % $Al_2O_3$, fluidity of the glass may deteriorate, whereby the leveling performance thereof falls at the time of the firing. As a result, a pinhole failure is likely to occur.

Moreover, in the light of heat resistance of the glass coat 30 and an environmental protection, the glass coat 30 preferably includes no Pb.

Further, the glass coat 30 is not limited to amorphous glasses. For example, the glass slurry preferably contains 2 to 35 mass % nucleation agent (one or more types selected from $TiO_2$, $ZrO_2$, $Fe_2O_3$, $V_2O_5$, NiO, $Cr_2O_3$, Pt and Au) because the slurry becomes a crystallized glass after firing, and exhibits improved heat resistance. The crystallized glass has a behavior that a glass transition point thereof, which serves as a thermal reaction, can be measured by a DTA (differential thermal analysis) before firing. However, once it is fired (e.g., at 900 degrees C.) and crystallized, no thermal reaction can be measured by the DTA at a temperature range (±100 degrees C.) similar to at least the glass transition point before firing.

Examples of the glass compositions containing a nucleation agent include silica powder: 18 mass %, alkaline earth oxide: 23 mass %, $TiO_2$ (nucleation agent): 23 mass %, rare earth oxide: 17 mass %, ZnO: 16 mass %, and $B_2O_3$: 3 mass %. In addition, examples of a rare earth oxide include, but not limited to, $La_2O_3$, $Y_2O_3$, $CeO_2$, $Pr_6O_{11}$, and $Nd_2O_3$, however, $La_2O_3$ is preferable.

Next, the cross-sectional configuration of the front end side of the $NO_x$ sensor element 10 will be described with reference to FIG. 3.

The $NO_x$ sensor element 10 has a configuration in which the first solid electrolyte layer 11a, the insulating layer 14a, the second solid electrolyte layer 12a, the insulating layer 14b, the third solid electrolyte layer 13a and the insulating layers 14c, 14d are laminated in this order. A detection chamber 16 is formed between the first solid electrolyte layer 11a and the second solid electrolyte layer 12a having a space therebetween. A gas GM to be measured is externally introduced into the detection chamber 16 via a first diffusion resistor 15a disposed at the left end (inlet) of the detection chamber 16.

A measuring chamber 18 is formed at the right of the detection chamber 16 and communicates with the detection chamber 16 via a second diffusion resistor 15b. The measuring chamber 18 extends through the second solid electrolyte layer 12a and is formed between the first solid electrolyte layer 11a and the third solid electrolyte layer 13a.

Here, the detection chamber 16 corresponds to a "space" in the claims.

A long plate-like heat-generating portion 50a is embedded between the insulating layers 14c and 14d and extends along the longitudinal direction. The heat-generating portion 50a heats the detection element 20 to a predetermined activation temperature for stabilizing operation through enhancement of oxygen ion conductivity of the solid electrolyte layers 11a to 13a. The heat-generating portion 50a is supported by the insulating layers 14c and 14d and constitutes the heater 50 on the whole. The heat-generating portion 50a is at least disposed in a position corresponding to the detection electrode 12b in the longitudinal direction (i.e., the axial direction O) of the $NO_x$ sensor 200 ($NO_x$ sensor element 10). A "position corresponding" means that the heat-generating portion 50a overlaps with a part of the detection electrode 12b in the longitudinal direction of the $NO_x$ sensor element 10. That is, as long as the heat-generating portion 50a overlaps with at least a part of the detection electrode 12b, because the heater 50 can operate to suitably control the temperature of the detection electrode 12b, the other part of the heat-generating portion 50a may be located at the rear end side with respect to the rear end of the detection electrode 12b, or may be located at the front end side with respect to the front end of the detection electrode 12b. The temperature of the detection electrode 12b preferably falls within a range from, for example, 600 to 700 degrees C. so as to stabilize the operation of each solid electrolyte layers 11a to 13a and to burn off the soot adhered to the surface of the detection electrode 12b. In addition, the insulating layers 14a to 14d are made of alumina as a main component, and the first diffusion resistor 15a and the second diffusion resistor 15b is made of a porous material, such as alumina. Furthermore, the heat-generating portion 50a is made of platinum or the like.

A oxygen pumping cell 11 includes the first solid electrolyte layer 11a made of zirconia, which has oxygen ion conductivity, as a main component, an inner first pump electrode 11c, and a first counter electrode (outer first pump electrode) 11b, which is a counter electrode of the inner first pump electrode 11c. The inner first pump electrode 11c and the outer first pump electrode 11b are disposed in such a manner as to hold the first solid electrolyte layer 11a therebetween. The inner first pump electrode 11c faces the detection chamber 16. Platinum is predominantly used to form the inner first pump electrode 11c and the outer first pump electrode 11b. Each surface of the electrodes is covered with a protection layer 11e, 11d made of a porous material. The inner first pump electrode 11c and the outer first pump electrode 11b correspond to a "pair of first pump electrode" in the claims.

The oxygen concentration detection cell 12 includes the second solid electrolyte layer 12a made of zirconia as a main component, the detection electrode 12b and a reference electrode 12c. The detection electrode 12b and the reference electrode 12c are disposed in such a manner as to hold the second solid electrolyte layer 12a therebetween. The detection electrode 12b is located downstream of the inner first pump electrode 11c and faces the detection chamber 16. Platinum is predominantly used to form the detection electrode 12b and the reference electrode 12c.

The insulating layer 14b has a cutout formed in such a manner as to accommodate the reference electrode 12c in contact with the second solid electrolyte layer 12a. The cutout is filled with a porous material, thereby forming a reference oxygen chamber 17. Application of extremely weak constant current to the oxygen concentration detection cell 12 causes oxygen to be sent into the reference oxygen chamber 17 from the detection chamber 16. By this procedure, the circumference of the reference electrode 12c is made into an oxygen concentration atmosphere that serves as a reference oxygen concentration.

The second oxygen pumping cell 13 includes a third solid electrolyte layer 13a made of zirconia as a main component, an inner second pump electrode 13b disposed on a surface of the third solid electrolyte layer 13a which faces the measuring chamber 18, and a second counter electrode (counter second pump electrode) 13c, which is a counter electrode of the inner second pump electrode 13b. Platinum is predominantly used to form the inner second pump electrode 13b and the counter second pump electrode 13c.

In addition, the counter second pump electrode 13c is disposed on a portion of the third solid electrolyte layer 13a which corresponds to the cutout of the insulating layer 14b, and faces the reference electrode 12c with the reference oxygen chamber 17 therebetween. The inner second pump electrode 13b and the counter second pump electrode 13c correspond to a "pair of second pump electrode" in the claims. The third solid electrolyte layer 13a corresponds to a "third solid electrolyte body" in the claims.

Next, an example operation of the $NO_x$ sensor element 10 is described. First, when an engine gets started, a control unit (not illustrated) is started. The control unit supplies power to the heat-generating portion 50a. The heat-generating portion 50a heats the first pumping cell 11, the oxygen concentration detection cell 12, and the second pumping cell 13 to an activation temperature. When each cell 11 to 13 is heated to the activation temperature, the first pumping cell 11 pumps out excess oxygen contained in a gas GM to be measured (exhaust gas) which is introduced into the detection chamber 16, from the inner first pump electrode 11c toward the first counter electrode 11b.

At this time, the oxygen concentration in the detection chamber 16 corresponds to an electric motive force (electrode-to-electrode voltage) Vs produced between the electrodes of the oxygen concentration detector cell 12. Thus, by controlling the direction and the magnitude of current of the first pump current Ip1 that energizes the first oxygen pumping cell 11 so that the electrode-to-electrode voltage of the oxygen concentration detection cell 12 becomes a constant voltage V1 (e.g., 425 mV), the oxygen concentration of the detection chamber 16 is adjusted to a predetermined low oxygen concentration.

The gas GN to be measured whose oxygen concentration has been adjusted flows toward the measuring chamber 18. Some voltage is applied to the second oxygen pumping cell 13. This voltage is set to such a constant voltage Vp2 as to cause decomposition of $NO_x$ contained in the gas GN to be measured into oxygen and nitrogen (e.g., 450 mV). By this application of voltage, $NO_x$ contained in the gas GN to be measured is decomposed into nitrogen and oxygen. Then, a second pump current Ip2 is applied to the second oxygen pumping cell 13 so as to pump out oxygen generated through decomposition of $NO_x$ from the measuring chamber 18. Since there is a substantially linear relationship between the second pump current Ip2 and the $NO_x$ concentration, through detection of the second pump current Ip2, the $NO_x$ concentration of the gas GN to be measured can be detected.

Figure 5:
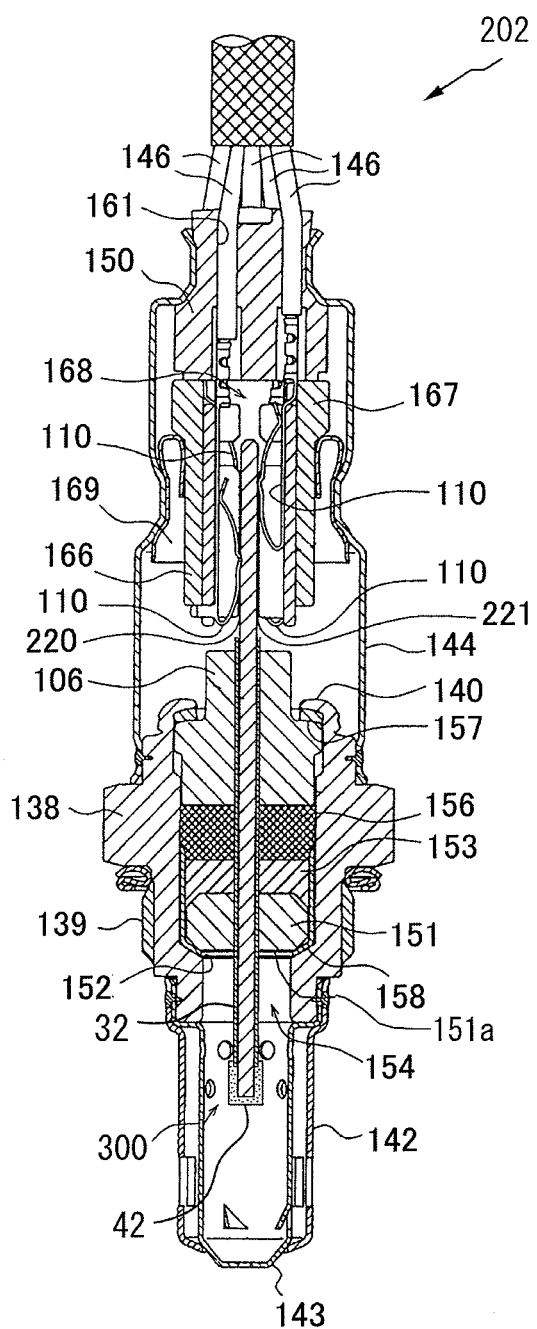
FIG. 5 is a sectional view of the $NO_x$ sensor in the longitudinal direction according to a second embodiment of the present invention.
Figure 6:
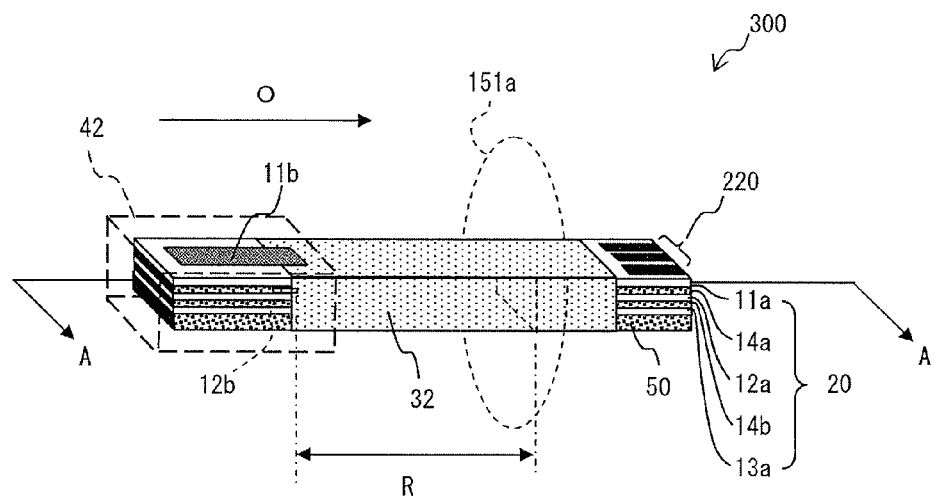
FIG. 6 is a perspective view of the $NO_x$ sensor element according to the second embodiment of the present invention.

FIG. 5 is a sectional view of an entire gas sensor ($NO_x$ sensor) 202 in the longitudinal direction according to a second embodiment of the present invention. FIG. 6 is a perspective view of a $NO_x$ sensor element 300. In addition, except for the $NO_x$ sensor element 300, since the gas sensor 202 according to the second embodiment has the same configuration as that of the gas sensor 200 according to the first embodiment, the same numerals are used for the identical configuration, and explanation thereof will be omitted.

In the $NO_x$ sensor element 300, as shown in FIG. 6, a glass coat 32 is formed on top and bottom surfaces (two faces adjacent to the above-mentioned side faces) of the detection element 20 beyond the region R, in addition to the side faces of the detection element 20.

Furthermore, a porous insulating ceramic layer 42 is formed on the front end side of the $NO_x$ sensor element 300. The porous insulating ceramic layer 42 externally covers the surface of the detection element 20 ($NO_x$ sensor element 300) and the front end surface of the glass coat 32, and also entirely covers the front end of the detection element 20. In addition, since the glass coat 32 has no air permeability, the glass coat 32 is not formed on the electrode 11b to avoid interfering the oxygen pumping. However, since the insulating ceramic layer 42 is porous (about 40% porosity) and has air permeability, it does not affect the oxygen pumping even if the electrode 11b is covered with the insulating ceramic layer 42.

In this way, by covering the front end portion of the glass coat 32 with the insulating ceramic layer 42, the glass coat 32 is prevented from being peeled off from the front end portion of the glass coat 32. As a result, improvement in durability of the glass coat 32 is achieved.

Figure 7:
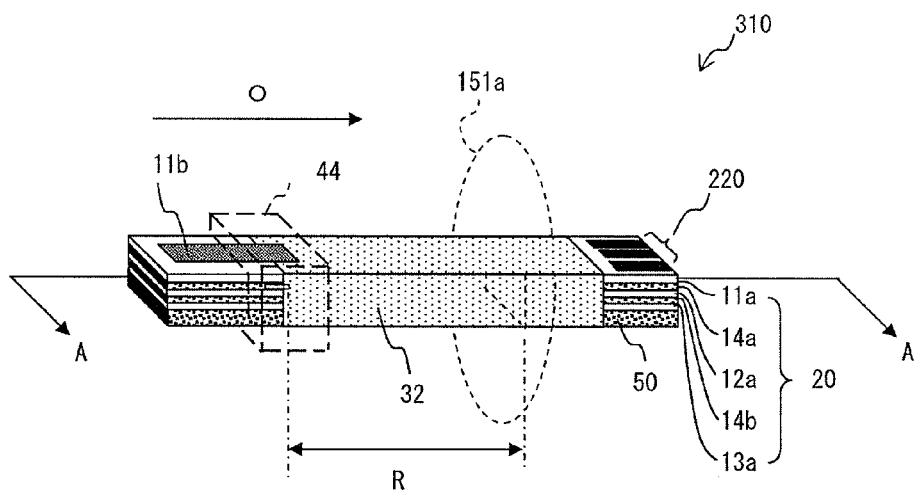
FIG. 7 is a perspective view of the $NO_x$ sensor in the longitudinal direction according to a third embodiment of the present invention.

FIG. 7 is a perspective view of a $NO_x$ sensor element 310 of the gas sensor ($NO_x$ sensor) according to a third embodiment of the present invention. Except for the $NO_x$ sensor element 310, since the gas sensor according to the third embodiment has the same configuration as that of the gas sensor 200 according to the first embodiment, an explanation and a diagram thereof will be omitted.

In the $NO_x$ sensor element 310, similar to the $NO_x$ sensor element 300, the glass coat 32 is formed on top and bottom surfaces (two faces adjacent to the above-mentioned side faces) of the detection element 20 beyond the region R in addition to the side faces of the detection element 20.

Furthermore, a porous insulating ceramic layer 44 is formed on the front end side of the $NO_x$ sensor element 310. The porous insulating ceramic layer 44 externally covers the surface of the detection element 20 ($NO_x$ sensor element 300) and the front end surface of the glass coat 32. However, although the insulating ceramic layer 44 covers the front end portion of the glass coat 32, it does not cover the front end side of the detection element 20 ($NO_x$ sensor element 310). Thus, the front end of the detection element 20 including the front end side of the electrode 11b is exposed.

According to the third embodiment, since at least the front end portion of the glass coat 32 is externally covered with the insulating ceramic layer 44, the front end portion of the glass coat 32 is prevented from being peeled off from the front end portion of the glass coat 32. As a result, improvement in durability of the glass coat 32 is achieved.

Notably, in FIGS. 5 and 6, the glass coat 32 covers four surfaces (top and bottom surfaces, and side surfaces) of the gas sensor element 300,310, and the insulating ceramic layer 42, 44 is formed so as to cover the front end portion of the glass coat 32. As shown in FIG. 2, when the top and bottom surfaces of the detection element 20 are covered with or constituted by the insulating layers, the glass coat 30 may be formed only on two side faces (right and left faces) where the solid electrolyte layer is exposed, and the insulating ceramic layer may be formed on the front end portion of the glass coat 30.

The present invention is not limited to the above-mentioned embodiment, and but may be embodied in various other forms without departing from the gist of the invention.

For example, in the above-mentioned embodiment, as shown in FIG. 3, the detection electrode 12b is disposed in the detection chamber 16 to which the inner first pump electrode 11c faces. However, the detection electrode 12b may be disposed in another chamber separated from the detection chamber 16. Such a configuration of the $NO_x$ sensor element is disclosed in, for example, JP2004-354400, A (FIG. 3). This $NO_x$ sensor element has a double-layered solid electrolyte layer. That is, in this configuration, the second solid electrolyte body 12a and the third solid electrolyte body 13a are disposed in the same solid electrolyte layer.

Similarly, the $NO_x$ sensor element may have a configuration where the first solid electrolyte body 11a and the third solid electrolyte body 13a are disposed in the same solid electrolyte layer.

Examples of the gas sensor can include an oxygen sensor, a $NO_x$ sensor or the like.

EMBODIMENT

Glass slurry containing the following composition was screen-printed on the side faces of the $NO_x$ sensor element having a composition described in the above embodiment. The glass slurry was applied in a single time so that a thickness thereof after drying process was to be 40 micrometers (20 micrometers after firing). Thereafter, the resultant was fired at 1000 degrees C. to thereby form a glass coat. The glass transition point of the glass coat was 750 degrees C. In addition, the thicknesses of the glass slurry and the glass coat were measured by a laser layer thickness meter, and the glass transition point of the glass coat was measured by the DTA (differential thermal analysis).

The glass slurry was formed such that glass powder containing silica powder: 60 mass %, alumina: 20 mass %, MgO: 5 mass %, and CaO: 15 mass % and butyl carbitol used for dispersant were wet-blended.

As a comparative sample, slurry made of 100 mass % alumina was applied in a single time to an alumina sheet and fired at 1500 degrees C. to thereby form an alumina coat.

The thus-obtained glass coat and alumina coat were subjected to an open pore measurement by the following method. The alumina coat showed an offset value of 0.09 microA, and it was regarded that the open pore was absence in the alumina coat. On the other hand, the glass coat showed an offset value of 0.01 microA, and it was regarded that no open pore exists therein. From these results, it was apparent that the glass coat with no open pore can be obtained in a single application. Measuring method for confirming existence/absence of open pore:

(1) The glass coat is formed on the side faces of the $NO_x$ sensor element, and thereafter, the heater 50 is energized so that resistance (impedance) of the first solid electrolyte body is to be 100 ohms. Subsequently, after the elapse of 600 seconds from the timing that the resistance of the first solid electrolyte body becomes 100 ohms, a second pump current Ip2 fed into a second oxygen pumping cell is measured as an offset value.

(2) Next, carbon is sprayed on the side faces of the NO$_x$ sensor element (including the glass coat) so that its thickness is to be 1 micrometer or more. This carbon coat contains 10 mass % or more carbon particles, each particle having a size of 1 micrometer or less.

(3) Further, the offset value of the NO$_x$ sensor element after the carbon coat is measured in the similar manner to (1). When the difference in the offset value before and after the carbon coat is less than 0.03 microA, it is considered no open pore exist in the glass coat.

Figure 4:
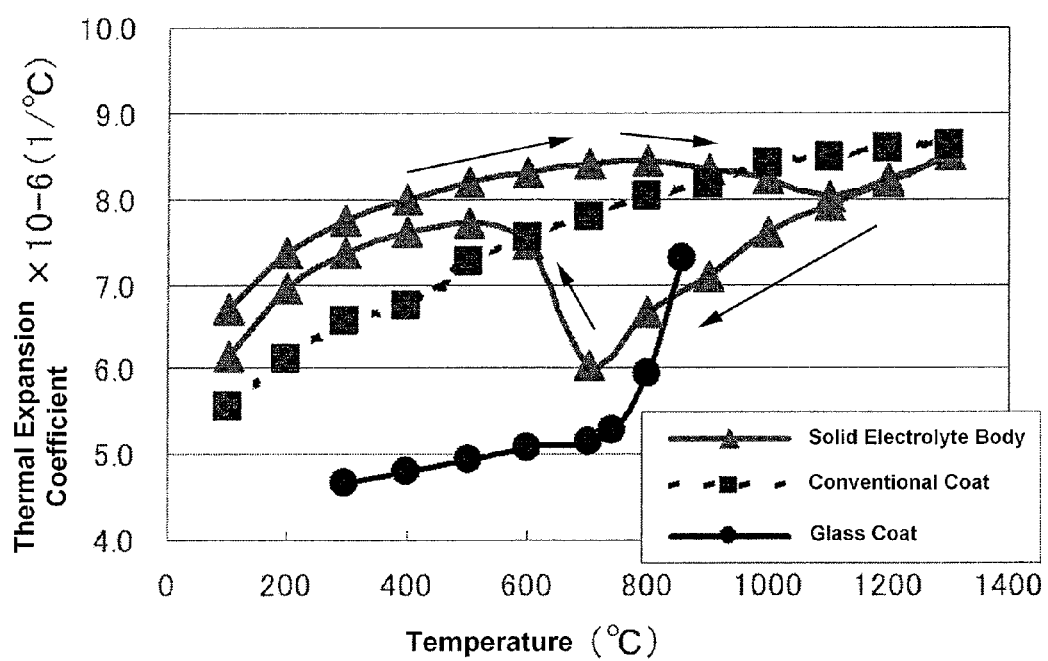
FIG. 4 shows temperature variations according to thermal expansion coefficient of a glass coat and an alumina coat.

Further, FIG. 4 shows temperature variations according to the thermal expansion coefficients of the solid electrolyte layer, the thus-formed glass coat and alumina coat. When compared at the same temperature, the thermal expansion coefficient of the glass coat was smaller than that of the alumina coat. This results exhibit that the glass coat is less likely to cause distortion of the detection element when the glass coat is fired or when the gas sensor is in use. In addition, thermo mechanical analyzer (TMA) was used for measuring the thermal expansion coefficient. In this measurement of thermal expansion coefficient, a bulk body having a predetermined size and a thickness was used as a sample. However, cut-out samples from a plurality of detection elements which correspond to the solid electrolyte body, the glass coat and the alumina coat, respectively, can be used for the measurement of thermal expansion coefficient.

DESCRIPTION OF REFERENCE NUMERALS 10, 300, 310: NO$_x$ sensor element (gas sensor element)
11: first oxygen pumping cell
11a: first solid electrolyte body
11b: the other side of first pump electrode
11c: one side of first pump electrode
12: oxygen concentration detection cell
12a: second solid electrolyte body
12b: detection electrode
12c: reference electrode
13: second oxygen pumping cell
13a: third solid electrolyte body
13b: the other side of second pump electrode
13c: one side of second pump electrode
16: space (detection chamber)
18: measuring chamber
20: detection element
30, 32: glass coat
42, 44: insulating ceramic layer
50: heater
50a: heat-generating portion
138: metallic shell (casing)
151: ceramic holder (inner member)
200: gas sensor

The invention claimed is:

1. A gas sensor, comprising:
a gas sensor element extending in a longitudinal direction and exposed to a gas to be measured at a front end side thereof;
a metal casing surrounding a radially outer circumference of the gas sensor element so that the front end side of the gas sensor element projects from a front end of the casing; and
an insulating inner member accommodated in the casing and surrounding the radially outer circumference of the gas sensor element,
wherein the gas sensor element includes a detection element in which a solid electrolyte body, a detection electrode disposed on the solid electrolyte body and exposed to the gas to be measured and a reference electrode disposed on the solid electrolyte body at a position corresponding to the detection electrode are provided,
wherein the gas sensor element further includes a heater laminated on the detection element and having therein an heat-generating portion that is disposed at an opposing position to at least the detection electrode in the longitudinal direction of the detection element,
wherein, in side faces of the detection element along a laminating direction where the solid electrolyte body and the heater are exposed to the gas to be measured, a region from a front end of the inner member to at least a part of the detection electrode along the longitudinal direction of the detection element is covered with a glass coat having a glass transition point of over 700 degrees C., and
wherein the detection electrode is controlled at a temperature range from 600 degrees C. or more to not more than the glass transition point of the glass coat.

2. The gas sensor according to claim 1,
wherein the glass coat contains Li, Na, K, Rb, Cs and Pb at a rate of 3000 mass ppm or less, respectively.

3. The gas sensor according to claim 1,
wherein an insulating ceramic layer is formed on a front end portion of the glass coat so as to externally cover the surface of the gas sensor element and that of the glass coat.

* * * * *